United States Patent

Heine et al.

[11] 3,937,722
[45] Feb. 10, 1976

[54] α-(CYANOETHYL)-BENZOIN ETHERS

[75] Inventors: Hans-Georg Heine, Krefeld; Hans Rudolph, Krefeld-Bockum; Karl Fuhr, Krefeld, all of Germany

[73] Assignee: Bayer AG, Germany

[22] Filed: Nov. 15, 1973

[21] Appl. No.: 416,041

Related U.S. Application Data

[60] Division of Ser. No. 163,470, July 16, 1971, which is a continuation-in-part of Ser. No. 885,985, Dec. 17, 1969, abandoned.

[30] Foreign Application Priority Data

Jan. 19, 1969  Germany............................ 1902051

[52] U.S. Cl....... 260/465 F; 260/340.5; 260/465 G; 260/465 R; 260/465 R; 260/470; 260/473 A; 260/558 S; 260/559 P; 260/591
[51] Int. Cl.²..................................... C07C 121/75
[58] Field of Search................................ 260/465 F

[56] References Cited
UNITED STATES PATENTS 3,821,277   6/1974   Koenig et al...................... 260/465

*Primary Examiner*—Lewis Gotts
*Assistant Examiner*—Dolph H. Torrence
*Attorney, Agent, or Firm*—Connolly and Hutz

[57] ABSTRACT

The invention relates to racemates of the formula (I)

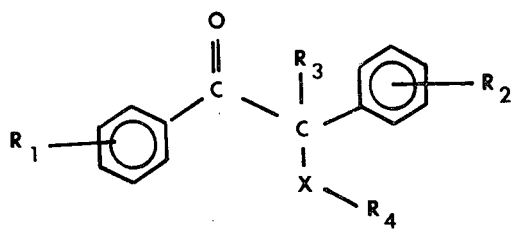

in which $R_1$ and $R_2$ are hydrogen, lower alkyl, methoxy, ethoxy or halogen, $R_3$ is unsubstituted alkyl or lower alkyl substituted with alkoxy carbonyl carbonamido, cyano or hydroxyl or unsubstituted alkenyl or alkenyl substituted with halogen or halogen-, methyl-, ethyl-, methoxy- or ethoxy-substituted phenyl or unsubstituted cycloalkyl or cycloalkyl substituted with lower alkyl or unsubstituted phenylalkyl or phenylalkyl, the phenyl nucleus of which being substituted with methyl, methoxy, halogen or nitro, and $R_4$ is unsubstituted alkyl or alkenyl or unsubstituted cycloalkyl or cycloalkyl substituted with lower alkyl or unsubstituted phenyl or phenyl substituted with lower alkyl methoxy, ethoxy or halogen or unsubstituted phenylalkyl or phenylalkyl, the phenyl nucleus of which being substituted with methyl, methoxy or halogen and X is oxygen or sulphur, which are useful as photosensitizers for light induced polymerisations of vinyl monomers as well as for the light induced crosslinking of unsaturated polycondensates and polymers.

3 Claims, No Drawings

-(CYANOETHYL)-BENZOIN ETHERS

CROSS REFERENCE TO RELATED APPLICATIONS

This application is a division of application Ser. No. 163,470 filed July 16, 1971, which, in turn, is a continuation-in-part of application Ser. No. 885,985 filed Dec. 17, 1969 and now abandoned.

It is possible to obtain α-substituted benzoins by reacting benzil with sodium amalgam and alkyl halides [J. Am. Chem. Soc., 56, 963 (1934)] or with Grignard reagents [Ber. 70 B, 23 (1937)]. The reaction of benzil or benzoin with carbonyl compounds also leads to α-substituted benzoins (Aldolen) [J. Chem. Soc. 67, 132 (1895) and Ber. 68, 2169 (1935)]. Furthermore, it is known to produce α-alkyl-benzoins by the reaction of benzoin with sodium alcoholates and subsequent alkylation with alkyl halides in benzene (U.S. Pat. No. 2,722,512). It is further known to prepare α-aryl-benzoin alkyl ethers by the reaction of α-aryl-desyl halides with alcohols [Ber. 39, 1278 (1906)] or with sodium alcoholates [J. Am. Chem. Soc. 76, 718 (1954)], or of aryl magnesium halides with α-phenylmandelic acid methyl ether [J. Am. Chem. Soc. 76, 2698 (1954)]. However, the only example of a synthesis of α-alkyl-benzoin alkyl ethers described is that of (−)α-methyl-benzoin methyl ether [J. Am. Chem. Soc. 81, 2748 (1959)]. Some α-substituted benzoin ethers in which the oxygen is attached via a methylene chain to the carbon atom standing in the α-position to the carbonyl group are likewise known [J. Org. Chem. 31, 1127 (1966); East German Patent Specification No. 57,857; and Ber. 100, 3266 (1967)].

In the processes mentioned above water must be completely excluded. The reactions take place at elevated temperatures and usually give only poor yields of the desired product. For the synthesis of (−) α-methyl-benzoin methyl ether, for example, mandelic acid methyl ether is reacted with lithium methyl to form the lithium salt which then gives the product with lithium phenyl in a yield of only 37 percent.

It has now been found that working in dimethyl sulphoxide (DMSO) as solvent at room temperature leads to 1. not only benzoin being converted in the presence of aqueous alkali with alkylating agents to form α-alkyl-benzoins in high yields, but also, depending on the concentration of the base and the alkylating agent, to a C- as well as a C- and O- or S-alkylation of the benzoin;
2. benzoin ethers and thio ethers preferably being C-alkylated under the same conditions; and
3. α-substituted benzoins being O- or S-alkylated.

The two-fold alkylation of the benzoin under the stated reaction conditions is unexpected. Likewise, the O-alkylation of α-substituted benzoins was not to be foreseen. Whereas alkylations in DMSO are normally carried out with the exclusion of water and in the presence of alkali metal hydrides or alcoholates (Na- or K-tert.-butylate), the alkylation of the benzoins and their derivatives succeeds in aqueous DMSO with alkali metal solutions to give good yields.

The object of the invention, therefore, comprises a process for the production of compounds of the formula (I)

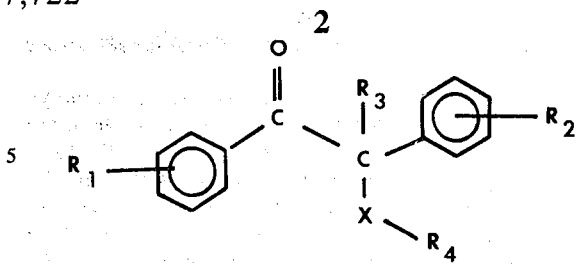

wherein
$R_1$ and $R_2$ are equal or different and are hydrogen, lower alkyl having up to about 4 carbon atoms, methoxy, ethoxy or halogen, $R_3$ is unsubstituted alkyl having up to about 12 carbon atoms or lower alkyl having up to about 4 carbon atoms and substituted with alkoxy carbonyl, the alkyl radical of which having up to about 4 carbon atoms, carbonamido, cyano or hydroxyl or unsubstituted alkenyl having 3 to about 6 carbon atoms or alkenyl having 3 to about 6 carbon atoms and substituted with halogen or halogen-, methyl-, ethyl-, methoxy- or ethoxy-substituted phenyl or unsubstituted cycloalkyl having 5 or 6 carbon atoms or cycloalkyl having 5 or 6 carbon atoms and substituted with lower alkyl having up to about 4 carbon atoms or unsubstituted phenyl or phenyl substituted with lower alkyl having up to about 4 carbon atoms, methoxy, ethoxy or halogen or unsubstituted phenylalkyl having 7 to about 10 carbon atoms or phenylalkyl having 7 to about 10 carbon atoms, the phenyl nucleus of which being substituted with methyl, methoxy, halogen or nitro, and $R_4$ is hydrogen or unsubstituted alkyl having up to about 12 carbon atoms or alkenyl having 3 to about 6 carbon atoms or unsubstituted cycloalkyl having 5 or 6 carbon atoms or cycloalkyl having 5 or 6 carbon atoms and substituted with lower alkyl having up to 4 carbon atoms or unsubstituted phenyl or phenyl substituted with lower alkyl having up to 4 carbon atoms, methoxy, ethoxy or halogen or unsubstituted phenylalkyl having 7 to about 10 carbon atoms or phenylalkyl having 7 to about 10 carbon atoms, the phenyl nucleus of which being substituted with methyl, methoxy or halogen and X is oxygen or sulphur,
which comprises reacting compounds of the formula (II)

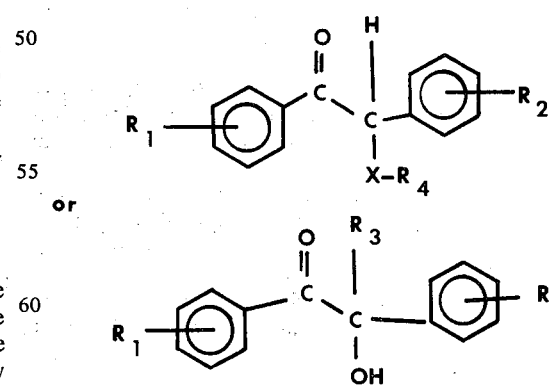

with electrophilic agents in the presence of basic catalysts in dipolar aprotonic solvents at temperatures of between about 0° and about 100°C, preferably between about 0° and about 30°C.

The use of dipolar aprotonic solvents as mentioned in the application allows to perform the alkylation reaction at especially low temperatures which allow to obtain very clean alkylation products in high yields (see table in Example 13).

In so far as $R_3$ is alkyl, alkenyl, cycloalkyl or aralkyl, and $R_4$ is alkyl, alkenyl, cycloalkyl, aryl or aralkyl, the compounds of the formula (I) are obtained in the form of the racemates which have not yet been described.

The following benzoins, for example, can be used as starting material: benzoin, 4,4'-dichlorobenzoin, 2,2'-dimethylbenzoin, 4,4'-dimethoxy-benzoin, 4,4'-dimethyl-benzoin, 4-methoxy-benzoin, 4-methyl-benzoin, 4,4'-diethyl-benzoin, 4,4'-diisopropyl-benzoin, 4,4'-diethoxy-benzoin, 3,3',4,4'-tetramethoxy-benzoin, 3,4,3',4'-bismethylenedioxy-benzoin, 4-bromobenzoin and 2'-chloro-3,4-dimethoxy-benzoin.

Examples of α-substituted benzoins which can be used according to the invention are α-methyl-, α-ethyl-, α-propyl-, α-butyl-, α-allyl-, α-benzyl- and α-phenylbenzoin; 4,4'-dichloro-α-methyl-benzoin, 4,4'-dimethyl-α-methyl-benzoin, 4,4'-dichloro-α-allyl-benzoin, 4,4'-dimethyl-α-allyl-benzoin, 4,4'-dimethoxy-α-methyl-benzoin, 4,4'-dimethoxy-α-allyl-benzoin and α-cinnamyl-benzoin, α-dodecyl-benzoin, α-isopropylbenzoin, α-(2-chloroallyl)-benzoin, α-(p-chlorobenzyl)-benzoin, α-(2-carbonamido)-benzoin and α-(p-xylyl)-benzoin.

Suitable benzoin ethers and thioethers are, for example: benzoin-methyl ether, -ethyl ether, -i-propyl ether, -propyl ether, -phenyl ether and -cyclohexyl ether; anisoin methyl ether, 4,4'-dimethylbenzoin ethyl ether and desyldodecyl sulphide, desyl-phenyl sulphide, benzoin-n-hexylether, benzoin-isobutylether, benzoin-p-chlorophenylether, benzoin-p-cresylether and desyl-p-chlorophenylsulfide.

The dipolar aprotonic solvents comprise, for example, dimethyl sulphoxide, diethyl sulphoxide, tetramethyl-sulphone, dimethyl formamide, dimethyl acetamide, hexamethyl-phosphoric acid triamide.

Electrophilic agents are, for example, 1. alkylating or aralkylating agents, for example: methyl iodide, ethyl bromide, butyl iodide, allyl chloride, propargyl chloride, benzyl chloride, 3-phenyl-propyl bromide, cinnamyl chloride, benzene-sulphonic acid ethyl ester, p-toluene-sulphonic acid methyl ester and α-halogen ether, and
2. Michael acceptors, e.g. α,β-unsaturated carbonyl compounds or nitriles, such as acrylonitrile, acrylic acid ethyl ester, crotonic acid methyl ester, acrylamide, croton nitrile, methyl vinyl ketone and benzalacetophenone.

As basic catalysts there may be used, for example, alkali metal and alkaline earth metal hydroxides, alkali metal carbonates and bicarbonates, and alkali metal alcoholates.

The concentration of the base may vary between about $10^{-3}$ and about 3 times the equivalent amount, that of the alkylating agent between about 1 and about 3 times the equivalent amount.

The reaction may be carried out in aqueous as well as in absolute solvents, optionally with the addition of further solvents, such as dioxan, benzene and tert.-butanol.

The reaction in sulphoxides in the presence of aqueous alkali metal solutions is particularly advantageous.

To carry out the process, the substrate to be reacted is expediently dissolved in one of the stated solvents, preferably DMSO, in a nitrogen atmosphere, and reacted at temperatures of between about 20°C and about 30°C in the presence of the required amount of alkali, preferably an aqueous 10–30 percent by weight alkali metal hydroxide solution, with the alkylating agent, while stirring. The speed of the reaction is affected by the type of the alkylating agent. The necessary reaction time generally lies between about 1 and about 24 hours.

Starting from benzoin, it is also possible to produce differently substituted α-alkyl-benzoin alkyl ethers, e.g. α-alkyl-benzoin methyl ethers, in one batch by using alkylating agents of different electrophilic character.

The α-substituted benzoins and benzoin ethers which are easily obtainable according to the process of the invention can be used as photosensitizers for light-induced polymerisations of vinyl monomers as well as for the light-induced cross-linking of unsaturated polycondensates and polymers. (See Examples 15 and 16).

The invention also relates to compounds of formula (I) wherein $R_1$, $R_2$ have the significance as defined above, $R_3$ has the significance as defined above except for unsubstituted and substituted phenyl, and $R_4$ has the significance as defined above except hydrogen.

EXAMPLE 1

α-Allyl-benzoin 90 ml of a 10% by weight aqueous sodium hydroxide solution are added with cooling in a nitrogen atmosphere to a solution of 42.4 g (0.2 mol) benzoin in 400 ml DMSO, and 22 ml (0.27 mol) allyl chloride are added dropwise at 20°C within 15 minutes. The reaction solution is further stirred for 2 hours and then poured into ice/water. The crystalline crude product (50 g) is recrystallised from petroleum ether and gives 37.9 g (75% of theory) α-allyl-benzoin of melting point 89°–93°C. A further 5.1 g of melting point 85°–90°C are obtained from the mother liquor.

| $C_{17}H_{16}O_2$ (252.30) | % C | % H | % O |
|---|---|---|---|
| calculated: | 80.92; | 6.39; | 12.68 |
| found: | 80.90; | 6.27; | 12.80 |

EXAMPLE 2

α-Methyl-benzoin

To a solution of 21.2 g (0.1 mol) benzoin in 200 ml DMSO there are added at 25°C 44 ml of a 10 % by weight sodium hydroxide solution and then 14.6 g (0.11 mol) methyl iodide. After stirring for 2 hours, the reaction mixture is poured onto ice and extracted with petroleum ether/ether. After working up in the usual way, there are obtained 24.2 g of a yellow oil which is filtered through silica gel/petroleum ether. There are subsequently eluted 1. 5.2 g (22%) α-methyl-benzoin methyl ether, $n_D^{25}$ = 1.5683;
2. 14.8 g (68%) α-methyl-benzoin, m.p. 66° – 67° C; and
3. 2.1 g. of a mixture of α-methyl-benzoin/benzoin.

EXAMPLE 3

α-Methyl-benzoin methyl ether

To a solution of 21.2 g (0.1 mol) benzoin in 200 ml DMSO there are added at 20°C 90 ml of a 10% by weight sodium hydroxide solution and subsequently 30 g (0.21 mol) methyl iodine. After stirring for 2 hours, the mixture is poured into ice/water, extracted with petroleum ether and worked up. The residue (22.5 g) is fractionated in a vacuum. There are obtained 1. 0.6 g of b.p. 80° – 126°C / 0.55 mm Hg, $n_D^{25}$ = 1.548;
2. 16.6 g of b.p. 126° – 129°C / 0.55 mm Hg, $n_D^{25}$ = 1.572; and
3. 3.4 g of b.p. 133° – 135°C / 0.55 mm Hg, cryst. m.p. 60° – 65°C.

Fraction (2) is recrystallised from petroleum ether and yields 12.7 g α-methyl-benzoin methyl ether, m.p. 35°C.

| $C_{16}H_{16}O_2$ (240.29) | % C | % H | % O |
|---|---|---|---|
| calculated: | 79.97; | 6.71; | 13.32 |
| found: | 80.0; | 6.61; | 13.7 |

EXAMPLE 4

α-Methyl-benzoin methyl ether 5.7 g (2.5 . $10^{-2}$ mol) α-methyl-benzoin are reacted in 50 ml DMSO at room temperature with 5 g (2.8 . $10^{-2}$ mol) p-toluene-sulphonic acid methyl ester in the presence of 11 ml of a 10% by weight sodium hydroxide solution. The crude product is filtered through silica gel/petroleum ether and yields, besides 0.95 g (17% of theory) of educt, 4.8 g (80% of theory) α-methyl-benzoin methyl ether of m.p. 36° – 38°C (petroleum ether).

| $C_{16}H_{16}O_2$ (240.29) | % C | % H | % O |
|---|---|---|---|
| calculated: | 79.97 | 6.71 | 13.32 |
| found: | 79.90 | 6.86 | 13.60 |

EXAMPLE 5

α-Hydroxymethyl-benzoin

From 21.2 g (0.1 mol) benzoin and 10 g (0.125 mol) chloro-dimethyl ether in 200 ml DMSO there are isolated in the presence of 45 ml of a 10% by weight sodium hydroxide solution after a reaction time of 1 hour at room temperature, 13.1 g (72% of theory) α-hydroxymethyl-benzoin of m.p. 85° – 86°C (ether/petroleum ether), besides 5.2 g (24%) of educt.

EXAMPLE 6

α-Methyl-benzoin methyl ether 22.6 g (0.1 mol) benzoin-methyl ether are reacted in 200 ml DMSO at room temperature with 7.5 g (0.12 mol) methyl iodide in the presence of 44 ml of a 10% by weight sodium hydroxide solution. The crude product is worked up after 2 hours. After a filtration through silica gel/petroleum ether, there are isolated 13.6 g (60% of theory) α-methyl-benzoin methyl ether of m.p. 35° – 36°C (petroleum ether).

EXAMPLE 7

α-(2-Carbethoxy-ethyl)-benzoin-i-propyl ether 1 ml of an aqueous 4N sodium hydroxide solution is added to a solution of 25.4 g (0.1 mol) benzoin isopropyl ether in 100 ml DMSO. The blue-green solution is mixed dropwise at 20°C with acrylic acid ethyl ester until the colour turns yellow (0.104 mol). After stirring for 2 hours, the product is worked up. The crystalline crude product is recrystallised from petroleum ether; melting point 52°–53°C. 86% of theory.

| $C_{22}H_{26}O_4$ (354.43) | % C | % H | % O |
|---|---|---|---|
| calculated: | 74.55 | 7.39 | 18.06 |
| found: | 74.30 | 7.38 | 18.10 |

EXAMPLE 8

α-(2-Cyanoethyl)-benzoin isopropyl ether

From 25.4 g (0.1 mol) benzoin isopropyl ether and acrylonitrile there are obtained in analogy with Example 7, 26.3 g (86% of theory) α-(2-cyanoethyl)-benzoin isopropyl ether of m.p. 67°–68°C (petroleum ether).

| $C_{20}H_{21}O_2$ (307,38) | % C | % H | % O | % N |
|---|---|---|---|---|
| calculated: | 78.14 | 6.89 | 10.41 | 4.56 |
| found: | 78.20 | 6.74 | 10.50 | 4.57 |

EXAMPLE 9

α-Methyl-benzoin allyl ether

From 5.7 g (2.5 . $10^{-2}$ mol) α-methyl-benzoin there are obtained in analogy with Example 4, with 3.44 ml (2.5 . $10^{-2}$ mol) allyl chloride in the presence of 11 ml of a 10% by weight sodium hydroxide solution, besides 3.0 g (53% of theory) of educt, 2.4 g (36% of theory) of a coulourless oil; b.p. 160°C/0.4 mm Hg, $n_D^{25}$ = 1.5594.

| $C_{18}H_{18}O_2$ (266.32) | % C | % H |
|---|---|---|
| calculated: | 81.17 | 6.81 |
| found: | 80.8 | 6.84 |

EXAMPLE 10

α-Phenyl-benzoin methyl ether 23 ml of a 10% by weight aqueous sodium hydroxide solution are added to 14.4 g (0.05 mol) α-phenyl-benzoin in 100 ml DMSO. 10.2 g p-toluene-sulphonic acid methyl ester dissolved in 20 ml DMSO are added dropwise at 20°–25°C. After stirring for 2 hours, the reaction mixture is worked up. The crude product (17.1 g) is chromatographed through silica gel/petroleum ether. Besides 7.8 g of educt + tosyl ester, there are obtained 9.3 g of a coulourless oil which crystallises upon the addition of methanol; m.p. 90° – 91°C (no depression of the melting point with authentic material).

EXAMPLE 11

α-Methyl-benzoin phenyl ether 18 g benzoin-phenyl ether are reacted in 200 ml DMSO with 25 g of a 10% by weight aqueous sodium hydroxide solution and 11.8 g methyl iodide at 20°C. After working up and filtering through silica gel/benzene, there are obtained, besides 6.2 g of educt, 11.8 g α-methyl-benzoin phenyl ether of m.p. 91.5°C (ethanol).

EXAMPLE 12

α-Methyl-desyl-phenyl sulphide

In analogy with Example 11, 30.4 g desyl-phenyl sulphide are reacted in 320 ml DMSO with 40 g of a 10% by weight aqueous sodium hydroxide solution and 18.9 g methyl iodide at room temperature. After working up, the crude product (21.6 g) is recrystallised twice from ethanol. 9 g α-methyl-desyl-phenyl sulphide of m.p. 101°C are obtained.

EXAMPLE 13

α-Methyl-benzoin methyl ether

Portions of 2.85 g α-methyl-benzoin are dissolved in a nitrogen atmosphere in 25 ml of solvent and mixed with 5.5 ml of a 10% by weight sodium hydroxide solution and then with 0.8 ml methyl iodide, while maintaining a temperature of 25°C. After stirring for 2 hours, the reaction products are poured into water, isolated and analysed by NMR-spectroscopy.

| Solvent | Crude product | % O-alkylation |
|---|---|---|
| ethanol | 2.8 g cryst. | 0 |
| dioxan | 2.75 g cryst. | 0 |
| acetonitrile | 2.8 g cryst. | 0 |
| hexamethyl-phosphoric acid triamide | 3.0 g part cryst. | 21 |
| tetramethylenesulphon | 2.65 g cryst. | 23 |
| dimethyl formamide | 3.0 g colourless oil | 47 |

-continued

| Solvent | Crude product | % O-alkylation |
|---|---|---|
| dimethyl sulphoxide | 2.95 g yellowish oil | 93 |

The following compounds were also prepared according to the process of the invention

| | |
|---|---|
| α-ethyl-benzoin | |
| α-butyl-benzoin | |
| α-benzyl-benzoin | |
| α-propargyl-benzoin | m.p. = 100 – 101°C |
| 4,4'-dichloro-α-methyl-benzoin | m.p. 89.5 – 90.5°C |
| 2,2'-dimethyl-α-allyl-benzoin | $n_D^{30}$ = 1.5712 |
| 4,4'-dimethoxy-α-allyl-benzoin | m.p. 119 = 122°C |
| α-(2-carbonamido ethyl)-benzoin | m.p. 150 = 152°C |
| α-ethyl-benzoin ethyl ether | $n_D^{20}$ = 1.5470 |
| α-allyl-benzoin ethyl ether | $n_D^{20}$ = 1.5596 |
| α-allyl-benzoin-i-propyl ether | $n_D^{20}$ = 1.5520 |
| α-methyl-benzoin-allyl ether | $n_D^{25}$ = 1.5594 |
| α-methyl-benzoin ethyl ether | $n_D^{30}$ = 1.5538 |
| α-benzyl-benzoin methyl ether | m.p. = 124 – 126°C |
| 4,4'-dichloro-α-methyl-benzoin methyl ether | $n_D^{30}$ = 1.5818 |
| α-n-butyl-benzoin-n-butyl ether | m.p. = 72 – 73.5°C |
| α-[2-carbethoxyethyl]-benzoin ethyl ether | $n_D^{25}$ = 1.5402 |
| α-(2-cyanoethyl)-benzoin ethyl ether | m.p. = 66 – 68°C |
| α-cinnamyl-benzoin | m.p. = 132 – 134°C |
| α-n-hexyl-benzoin | m.p. = 71.5 – 73°C |
| α-i-propyl-benzoin | m.p. = 103 – 104.5°C |
| α-methyl-benzoin cyclohexyl ether | $n_D^{20}$ = 1.5676 |
| α-benzyl-benzoin ethyl ether | m.p. = 100 – 101°C |
| α-[2-cyanoethyl]-benzoin methyl ether | m.p. = 88 – 89°C |
| α-(2-cyanoethyl)-benzoin methyl ether | m.p. 87 – 88.5 |
| α-(2-cyanoethyl)-benzoin n-propyl ether | 76 – 78 |
| α-(2-cyanoethyl)-benzoin n-butyl ether | 56 – 57 |
| α-(2-cyanoethyl)-benzoin cyclohexyl ether | 143 – 144 |
| α-(2-cyanoethyl)-benzoin phenyl ether | 113 – 115 |
| α-(2-carbomethoxyethyl)-benzoin methyl ether | 65 – 68 |
| α-(2-carbomethoxyethyl)-benzoin ethyl ether | 42 – 44 |
| α-(2-carbomethoxyethyl)-benzoin n-propyl ether | 53 – 55 |
| α-(2-carbomethoxyethyl)-benzoin i-propyl ether | 88 – 90 |
| α-(2-carbomethoxyethyl)-benzoin n-butyl ether | 58 – 61 |
| α-(2-carbomethoxyethyl)-benzoin cyclohexyl ether | 86 – 89 |
| α-(2-carbomethoxyethyl)-benzoin phenyl ether | 98 – 99 |
| α-(2-carbonamido-ethyl)-benzoin methyl ether | 187.5–188.5 |
| α-(2-carbonamido-ethyl)-benzoin ethyl ether | 153 – 155 |
| α-(2-carbonamido-ethyl)-benzoin n-propyl ether | 169 – 170 |
| α-(2-carbethoxyethyl)-benzoin cyclohexyl ether | 90 – 93 |

EXAMPLE 14

α-Allyl-benzoin methyl ether 66 ml of a 20% by weight sodium hydroxide solution are added dropwise at 20°–25°C to a solution of 63.6 g (0.3 mol) benzoin and 25.2 g (0.33 mol) allyl chloride in 500 ml DMSO. After 2 hours, 61.4 g (0.34 mol) p-toluene-sulphonic acid methyl ester and subsequently another 66 ml of the 20% sodium hydroxide solution are added dropwise to the reaction mixture. Working up after 24 hours yields 84.6 g of an oil the distillation of which gives 47 g (59%) α-allyl-benzoin methyl ether; b.p. 119° – 120°C/0.2 mm Hg, $n_D^{30}$ = 1.5640.

| $C_{18}H_{18}O_2$ (266.3) | % C | % H | % O |
|---|---|---|---|
| calculated: | 81.18 | 6.81 | 12.01 |
| found: | 81.20 | 6.78 | 12.30 |

EXAMPLE 15

0.1 g α-(β-carbethoxyethyl)-benzoin ethyl ether are added to 10 g of freshly distilled acrylic acid methyl ester and exposed with a mercury-vapour high-pressure burner (Philips HPK 125 W/L) through quartz glass in a water bath at 24°C. The solution of the sensitiser in the monomer is under nitrogen atmosphere in a quartz glass whose inner diameter is 1,7 cm. The exposure time is 2.5 minutes.

Immediately after exposure the quartz glass is introduced into an ice/common salt mixture to prevent heat polymerisation. The solution of the polymer in the monomer including the solid polymer parts, which are on the inner side of the quartz glass (on the side facing the mercury-vapour high-pressure burner), is rinsed with small amounts of a solvent (methylene chloride) in a small round-bottomed flask. Thereafter non-polymerised parts and the solvent are distilled off in a rotary evaporator. After drying in the vacuum drying chamber at 60°C to constant weight, the amount of the polymer is determined. It amounts to 11.8 percent by weight. If the sensitiser is not present, the polymer amount is below 0.1 percent.

EXAMPLE 16

0.1 g α-methyl benzoin methyl ether is added to 10 g each of the vinyl monomers given in the Table and together with the corresponding samples, which do not contain a sensitiser, are exposed in test tubes (16 cm × 1,5 cm) under nitrogen in the photochemical reactor PR-20 of the firm of SEM Bruckl (Munich) at 20° whilst using a GWCa filter glass tube (above λ = 330 nm translucent) with a mercury high-pressure burner (Philips HPK 125W). The change in the samples during exposure is given in the Table.

Table

| Vinyl monomer | Properties of the exposed samples with sensitiser after min. | without sensitiser |
|---|---|---|
| Methyl acryl acid methyl ester | 5 solidified glass | 60 no change |
| Acrylonitrile | <5 colourless polymer | 60 no change |
| Acryloamide a) | <5 colourless polymer | 60 no change |
| 1.1-dichloro-ethylene | 15 colourless polymer | 30 no change |
| Vinyl acetate | 20 highly viscous solution | 60 no change | a) 25 % by weight solution in methanol

We claim:
1. A compound of the formula

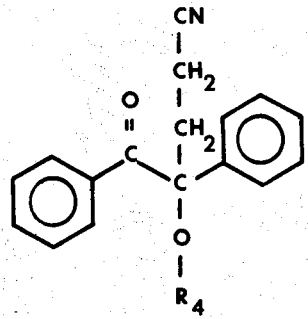

wherein $R_4$ is ethyl or isopropyl.
2. The compound of claim 1 wherein $R_4$ is ethyl.
3. The compound of claim 1 wherein $R_4$ is isopropyl.

* * * * *